United States Patent [19]

Zimerman

[11] 4,326,511
[45] Apr. 27, 1982

[54] INTRAUTERINE CONTRACEPTIVE DEVICE

[76] Inventor: Clota E. Zimerman, 9 de Julio 532-A, Cordoba, Argentina

[21] Appl. No.: 82,283

[22] Filed: Oct. 5, 1979

[51] Int. Cl.³ ............................................. A61F 5/46
[52] U.S. Cl. ................................................... 128/130
[58] Field of Search ........................................ 128/130

[56] References Cited

U.S. PATENT DOCUMENTS

| | | | |
|---|---|---|---|
| 3,454,004 | 7/1969 | Leininger et al. | 128/130 |
| 3,467,089 | 9/1969 | Hasson | 128/130 |
| 3,654,258 | 2/1972 | Massouras | 128/130 |
| 3,935,860 | 2/1976 | Hoff | 128/130 |
| 3,957,042 | 5/1976 | Krzaklewski et al. | 128/130 |
| 4,026,281 | 5/1977 | Mayberry et al. | 128/130 |
| 4,198,966 | 4/1980 | Kaivola | 128/130 |

*Primary Examiner*—John D. Yasko
*Attorney, Agent, or Firm*—John S. Roberts, Jr.

[57] ABSTRACT

Disclosed is an intrauterine device contraceptive to avoid pregnancy.

The device comprises a vector and contraceptor, said vector consisting of a vertical stem having two horizontal arms, the arm at the end of said vertical stem being longer than the second arm, said vertical stem being twisted by a copper wire having a surface area of above 200 square millimeters. The vertical stem is made from a plastic material, generally polyethylene.

The present intrauterine device contraceptive has the advantage of a complete reduction of the expulsion in view of its new particular shape.

4 Claims, 1 Drawing Figure

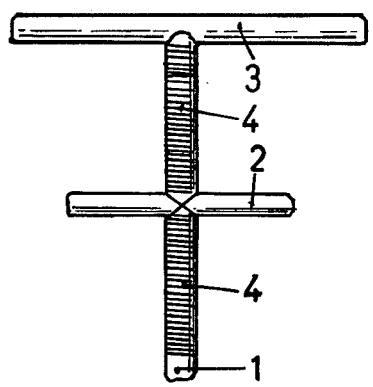

INTRAUTERINE CONTRACEPTIVE DEVICE

The present invention relates to an intrauterine device to avoid pregnancy. More particularly the invention relates to an intrauterine device contraceptive (hereinafter referred to as IUD).

Already in 1959 it was suggested to utilize IUD made of inert materials as contraceptive and the expected results were indeed obtained. Today the IUD is considered to be an ideal contraceptive. Although it requires a clincal procedure for its fixation, it rarely causes systenic hazards, and provides long-term protection against pregnancy. The known IUD which was rigorously tested and is being described in the prior art, consists normally from a plastic device having the shape of the letter T. Later on in 1969 Zipper et al. (Amer. Journal of Obstetrics and Gynecology, 105, 529-34, 1969) demonstrated the antifertility effect of copper ions. Extensive thorough explorations were subsequently done on twisting copper wire on the T device. The wire should be very thin in order to enable a large surface area, since copper ions are continuously released within the uterus. The mechanism to explain the copper influence is not yet fully elucidated. Apparently the contraceptive action of the copper is due to the release of the copper ions into the uterine cavity where they influence various biochemical reactions. Most likely, the copper ions influence the cationic antagonism specifically related to zinc. One of the most important zinc-containing enzymes in the female reproductive tract is carbonic anhydrase. Copper may compete with zinc and inhibit the carbonic anhydrase reaction, thus resisting implantation. It could certainly be stated that the copper wire changes the pH in the zone of the female reproductive tract from alkaline to acid, thus paralyzing the spermatozoon and avoiding pregnancy. In order to increase the useful life of such IUD, attempts have been made to increase the copper content of the device by its impregnation with metallic copper or copper salts such as copper carbonate or copper sulfate. However these attempts have not been successful because the copper is not released from the impregnated plastic device and therefore no effect was actually obtained.

One of the main disadvantages of the T-shaped intrauterine device is its repulsion from the uterus. Tests have been carried out looking for a better shape, without this disadvantage. Today there are indeed available on the market various copper IUD shapes, but in particular the 7-shape (patented and manufactured by G. D. Searle & Co.) and the Lippes loop IUD are most encountered. Although statistic data show that the new shapes may have a trend of better results than the T-shape device, it appears that there is a long felt need for an improved shape which could solve completely the repulsion problem. It is an object of the present invention to provide a new copper intrauterine contraceptive device which is completely free of expulsion. It is another object of the present invention to provide a new copper intrauterine contraceptive device which can be utilized for longer periods of time than the known copper IUD. Thus the invention consists of an intrauterine contraceptive device comprising a vector and contraceptor, said vector consisting of a vertical stem having two horizontal arms, the arm at end of said stem being longer than the second arm, said vertical stem being twisted by a copper wire having a surface area of above 200 square mm. It was found that the new copper IUD according to the present invention, reduces substantially to zero any incident due to its utilization. In particular, the new contraceptive device suppresses completely its expulsion, a fact which contributes to the prolonged safe use. The vector can be made from any plastic material, usually polyethylene or other flexible plastic materials to which a reagent is added to make it radio-opaque.

One of the main advantages of the present invention is the complete reduction of the expulsion, due to the new shape of the IUD and particularly to the second horizontal arm. This second horizontal arm, located about the middle of the vertical stem, imparts more stability to the intrauterine contraceptive device, providing a good support for it in the uterus wall.

BRIEF DESCRIPTION OF THE DRAWING

The FIGURE illustrates a preferred embodiment of the present invention.

According to a preferred embodiment according to the present invention, the copper wire contraceptor twisted around the vertical stem will have a surface area of at least 300 square mm and most preferably about 500 square mm. This feature enables the use of the contraceptive device for longer periods of time than these commonly known with a copper wire having a surface area of only 200 square mm. This embodiment solves the problem of increase in the useful life of the contraceptive device in a different approach from that attempted by the prior art of impregnating the plastic vector with copper salts. As already mentioned copper ions are constantly released from the wire and a larger surface area will increase accordingly the copper availability of the contraceptive intrauterine device according to the present invention. In order to avoid any infection in the uterus cavity, the copper from which the wire is made should be of a high purity, generally containing above 97% copper and most preferably about 98.7% copper. It was reported that copper IUD may offer some indirect prophylexis against genococcal infection. It was demonstrated in vitro research, that copper ions kill or inhibit growth of *Neisseria gonorrhoea*.

The size of the contraceptive device according to the present invention, does not differ from the known T- and 7-shaped devices, being generally about 35 mm length for the vertical stem and about the same size for the arm at the end of the stem. One of the requirements of the new contraceptive device according to the present invention is that the second arm which is normally located in the middle of the vertical stem, should be shorter than the second horizontal arm. The diameter of the vector is generally not more than 1.4 mm and preferably not more than 1.3 mm. This small diameter and the flexibility of the material from which the vector is made, cause a substantial decrease in the secondary symptoms such as: bleeding, pains, leucorrhoea etc.

While the invention has been described in connection with specific embodiments thereof, it will be understood that it is capable of further modifications and this patent is intended to cover any variation, uses, or adaptations of the invention following in general the principle of the invention and including such departures from the present disclosure as come within known or customary practice in the art to which the invention pertains and as may be applied to the essential features hereinbefore set forth and as fall within the scope of the invention. The following invention will be further illustrated by the attached FIGURE without being limited thereto. The intrauterine contraceptive device consists of a vertical vector (1) made of a plastic material, having two horizontal arms (2) and (3). The arm (3) is longer than arm (2). A copper wire (contraceptor) having a surface area of between 200-300 square mm, is twisted around the vertical vector (1).

The intrauterine device according to the present invention can be safely used for women as well as for animals such as cats, dogs etc.

I claim:

1. An intrauterine contraceptive device comprising a vector and contraceptor, said vector consisting of a vertical stem having two horizontal arms, the arm at the end of said stem being longer than the second arm, said vertical stem being twisted by a copper wire having a surface area of about 200-500 square mm wherein the second arm is located about the middle of the vertical stem and wherein said vertical stem is made from a plastic material.

2. An intrauterine contraceptive device according to claim 1, wherein said vertical stem has a diameter not greater than 1.3 mm.

3. An intrauterine contraceptive device according to claim 1, wherein said plastic material is polyethylene.

4. An intrauterine contraceptive device according to claim 1, wherein the wire is made from copper having a purity of about 98.7% copper.

* * * * *